US010394416B2

(12) United States Patent
Jeon et al.

(10) Patent No.: US 10,394,416 B2
(45) Date of Patent: Aug. 27, 2019

(54) USER INTERFACE SYSTEM AND METHOD FOR ENABLING MARK-BASED INTERACTION FOR IMAGES

(71) Applicant: Samsung Electronics Co., Ltd., Suwon-si, Gyeonggi-do (KR)

(72) Inventors: Joo-Hyuk Jeon, Seoul (KR); Yeong-Kyeong Seong, Yongin-si (KR); Ki-Yong Lee, Suwon-si (KR); Ye-Hoon Kim, Seoul (KR); Baek-Hwan Cho, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 446 days.

(21) Appl. No.: 15/109,022

(22) PCT Filed: May 16, 2014

(86) PCT No.: PCT/KR2014/004399
§ 371 (c)(1),
(2) Date: Jun. 29, 2016

(87) PCT Pub. No.: WO2015/102167
PCT Pub. Date: Jul. 9, 2015

(65) Prior Publication Data
US 2016/0334964 A1    Nov. 17, 2016

(30) Foreign Application Priority Data
Dec. 31, 2013 (KR) .......................... 10-2013-0168616

(51) Int. Cl.
*G06F 3/0482*    (2013.01)
*G06F 3/0481*    (2013.01)
(Continued)

(52) U.S. Cl.
CPC ............ *G06F 3/04815* (2013.01); *A61B 6/03* (2013.01); *A61B 6/463* (2013.01); *A61B 6/466* (2013.01);
(Continued)

(58) Field of Classification Search
CPC combination set(s) only.
See application file for complete search history.

(56) References Cited

U.S. PATENT DOCUMENTS

| 7,103,135 | B2 | 9/2006 | Koppe et al. |
| 8,051,386 | B2 | 11/2011 | Rosander et al. |
| 8,162,833 | B2 | 4/2012 | Zhang et al. |
| 2004/0070584 | A1* | 4/2004 | Pyo .......................... G06T 7/60 345/419 |

(Continued)

FOREIGN PATENT DOCUMENTS

| KR | 20020041277 A | 6/2002 |
| KR | 20050094536 A | 9/2005 |

(Continued)

*Primary Examiner* — Rayeez R Chowdhury
(74) *Attorney, Agent, or Firm* — Jefferson IP Law, LLP

(57) ABSTRACT

Disclosed is a user interface which enables mark based interaction for images. The present disclosure relates to a user interface which enables mark based interaction for images, the images comprising a volume which is a three-dimensional image and slices which are two-dimensional images, each of which represents a cross section of the volume. At least two of the images each include the same visual mark for identifying at least one common region of interest. The user interface comprises: an input unit for receiving a user input associated with the same visual mark included in one of the images; and at least one component for enabling the interaction for the images including the same visual mark associated with the user input.

16 Claims, 20 Drawing Sheets

(51) Int. Cl.

| | |
|---|---|
| *G06F 3/0484* | (2013.01) |
| *A61B 6/03* | (2006.01) |
| *A61B 6/00* | (2006.01) |
| *G06T 11/00* | (2006.01) |
| *G06T 15/08* | (2011.01) |
| *G06T 19/20* | (2011.01) |
| *G16H 30/40* | (2018.01) |
| *G16H 40/60* | (2018.01) |
| *G16H 50/20* | (2018.01) |

(52) U.S. Cl.
CPC ............ *A61B 6/468* (2013.01); *A61B 6/469* (2013.01); *G06F 3/0482* (2013.01); *G06F 3/04845* (2013.01); *G06T 11/00* (2013.01); *G06T 15/08* (2013.01); *G06T 19/20* (2013.01); *G16H 30/40* (2018.01); *G16H 40/60* (2018.01); *G16H 50/20* (2018.01); *A61B 6/502* (2013.01); *G06F 2203/04804* (2013.01); *G06T 2207/20104* (2013.01); *G06T 2207/20108* (2013.01)

(56) References Cited

U.S. PATENT DOCUMENTS

| | | | |
|---|---|---|---|
| 2007/0167763 A1* | 7/2007 | Hyun | A61B 8/08 600/437 |
| 2008/0009722 A1* | 1/2008 | Simopoulos | A61B 8/08 600/437 |
| 2010/0256492 A1 | 10/2010 | Lee et al. | |
| 2012/0076390 A1* | 3/2012 | Potts | G06T 7/0014 382/133 |
| 2012/0293514 A1* | 11/2012 | Virtue | G06T 7/174 345/424 |
| 2013/0331697 A1 | 12/2013 | Park et al. | |
| 2014/0037177 A1* | 2/2014 | Endo | G06T 11/00 382/131 |
| 2016/0217568 A1* | 7/2016 | Vancamberg | G06T 7/0012 |

FOREIGN PATENT DOCUMENTS

| | | |
|---|---|---|
| KR | 20100062838 A | 6/2010 |
| KR | 20130138612 A | 12/2013 |

* cited by examiner

USER INTERFACE SYSTEM AND METHOD FOR ENABLING MARK-BASED INTERACTION FOR IMAGES

TECHNICAL FIELD

The present disclosure relates to a user interface, and more specifically relates to a user interface for enabling interaction for images.

BACKGROUND ART

Recently, with the development of medical image obtaining and processing technology, lesions of a human body have been able to be diagnosed by using three-dimensional medical images. The three-dimensional medical images may be obtained, for example, by integrating a number of two-dimensional images to reconfigure a three-dimensional image, or may be obtained by photographing the medical image by using a three-dimensional scanner. In general, the three-dimensional image (that is, a stereoscopic image) may include a plurality of two-dimensional planar images that are included in a specific space. Therefore, the three-dimensional image may be expected to contain more information available for, for example, the diagnoses of the lesions, compared to the two-dimensional image that represents only a specific single plane.

In general, the medical imaging diagnosis sector handles a volume that is a three-dimensional image and slices that are cross sectional images obtained by cutting the volume on three planes, which are perpendicular to each other. The volume and the slices, which are cross sections thereof, may include the region of interest (ROI), such as lesions, in common.

DETAILED DESCRIPTION OF THE INVENTION

Technical Problem

The present disclosure provides a user interface that enables mark-based interaction for the volume and the slices, which are associated with each other.

Technical Solution

A user interface system for enabling mark-based interaction for images, which is provided according to one aspect, may be a user interface system for enabling mark-based interaction for images including a volume that is a three-dimensional image and slices that are two-dimensional images representing cross sections of the volume, wherein two or more of the images may contain the same visual mark for identifying one or more common regions of interest and the user interface system may include: an input unit configured to receive a user input that is associated with the same visual mark contained in one image among the images; and one or more components configured to enable interaction for the images containing the same visual mark associated with the user input.

In an embodiment, the mark may further contain at least one of text representations comprised of a combination of text, numbers, or symbols, which describe the region of interest, pictures, signs, or graphical representations, which intuitively represent the region of interest.

In another embodiment, one or more marks may be generated in the inside, or the outside, of the region of interest.

In another embodiment, the one or more components may include a mark generation unit that is configured to: generate a mark containing identification information for uniquely identifying the region of interest according to the user input; place the generated mark on the region of interest in one image among the images; then, automatically generate corresponding marks containing the same identification information as the mark, and tag the same on the corresponding regions of interest in other images rather than the one image among the images; and display, on a screen, the other images, which contain the mark for identifying the region of interest, rather than the one image among the images.

In another embodiment, the one or more components may include an image search unit that is configured to: receive user input information for selecting a mark of the region of interest in one image among the images; select slices according to predetermined selection criteria from the slices containing the region of interest identified by the mark that is selected by the user input information; and display the selected slices on a screen.

In another embodiment, the predetermined selection criteria, by which the image search unit selects the slices, may include at least one of: preferentially selecting the slice corresponding to the MPR (Multi-Planar Reconstruction) view based on the region of interest identified by the selected mark; preferentially selecting the slice with which the user has previously interacted; or preferentially selecting the slice that contains as many other regions of interest as possible in the volume.

In another embodiment, the one or more components may further include a mark arrangement unit that is configured to display the marks contained in the volume to not overlap each other.

In another embodiment, when the volume displayed on the screen is modified by enlarging, reducing, rotating, or moving the same, the mark arrangement unit may display the marks to not overlap each other while modifying the marks according to the modification of the volume.

In another embodiment, the one or more components may further include an ROI visualization unit that is configured to adjust image data representing the volume such that the selected region of interest or the region of interest identified by the selected mark among the regions of interest in the volume is visually distinct from the periphery.

In another embodiment, the ROI visualization unit may be configured to modify image data representing the volume such that the transparency of the peripheral area surrounding the selected region of interest, or the region of interest identified by the selected mark gradually increases as it goes further from the selected region of interest or the region of interest identified by the selected mark.

In addition, a user interface providing method for enabling mark-based interaction for images, which is provided according to another aspect, may be a user interface providing method for enabling mark-based interaction for images including a volume that is a three-dimensional image and slices that are two-dimensional images representing cross sections of the volume, wherein two or more of the images may contain the same visual mark for identifying one or more common regions of interest, and the method may include: receiving a user input that is associated with the same visual mark contained in one image among the images; and enabling interaction for the images containing the same visual mark associated with the user input.

The aforementioned aspects and embodiments, and other embodiments, will be described in more detail below with reference to the drawings.

Advantageous Effects

The present disclosure can implement a user interface that visually displays a mark having unique identification information in the region of interest (ROI), which is contained in common in the volume and the slices, which are associated with each other, and associates the volume and the slices based on the mark in order to thereby enable a variety of interactions, such as display, search, arrangement, and visualization.

MODE FOR CARRYING OUT THE INVENTION

Figure 1A:
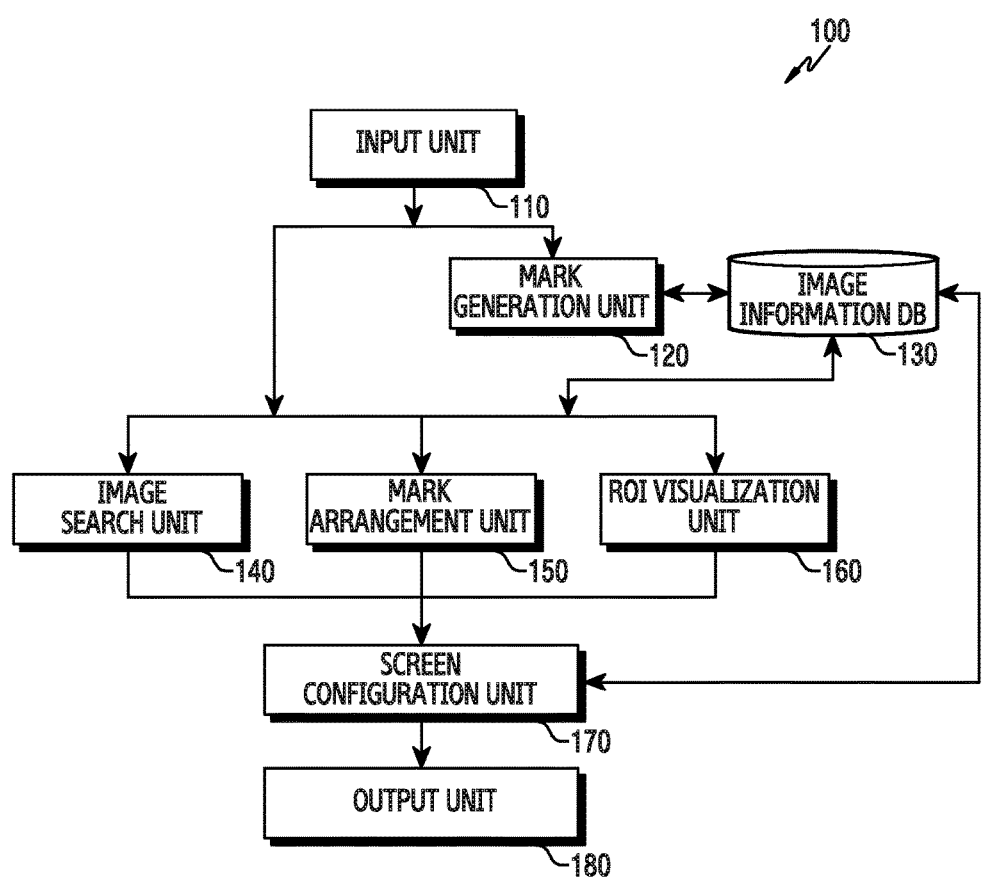
FIG. 1A is a block diagram illustrating an embodiment of a user interface system for enabling mark-based interaction for images.

Hereinafter, embodiments will be described in detail with reference to the accompanying drawings. In describing the present disclosure, a detailed description of known configurations or functions incorporated herein will be omitted when it is determined that the detailed description may make the subject matter of the present disclosure unnecessarily unclear. Further, terms as described below are defined in consideration of each function in the technology described herein, but may vary according to the intention of a user or operator or customs. Therefore, the terms should be substantially defined on the basis of the details throughout the specification.

Hereinafter, various embodiments of a user interface system and a method for enabling the mark-based interaction for images will be described with reference to the drawings.

An embodiment of a user interface system and a method for enabling the mark-based interaction for images may be used for diagnoses that are conducted through a computer aided diagnosis (CAD) system by using a volume and a plurality of slices that represent cross sections of the volume. The volume and the slices, for example, may be medical images obtained by photographing a certain person's breast for early detection of breast cancer in the field of an ultrasonic diagnosis. In this case, it is necessary for the user to separate a specific region of interest (ROI) in the images and to associate the same with each other in order to discover lesions related to, for example, the breast cancer.

The embodiment of a user interface system and a method for enabling the mark-based interaction for images may provide a user interface that allows the user to perform interaction with respect to the medical images comprised of a volume and slices.

The embodiment of a user interface providing system and a method may be implemented to include a computing device and an image processing application that is installed in the computing device and that is coded to be executed by a processor of the computing device in order to thereby display images on a display and in order to thereby receive a user input through a user input device.

The image processing application may include computer codes, modules, routines, instructions, software, programs, or applications, which are implemented to perform all or some of the operations of methods to be described below when being executed by a processor of the computing device. The computing device may include a processor, a memory, a display, and a user input device. The computing device may encompass a tablet PC, a laptop PC, a desktop PC, a server system, or a distributed computer system.

The image processing application is executed by the computing device in order to thereby provide a user interface. The user interface may enable a variety of interactions between the user and the image processing application that is executed by the computing device.

Hereinafter, for simple representation, a combination of the computing device and the image processing application for performing a variety of interactions with the user will be referred to as an "application". In addition, for simple representation, the user interface provided by the application in order to enable a variety of interactions will be referred to as a "user interface".

The user may perform an interaction with the application for images through the user interface. The user may perform a variety of interactions, such as generating, viewing, editing, marking, arranging, searching for, or storing images through the user interface.

In the case where a plurality of medical images are obtained by photographing the same region of a human body from different positions, even though the plurality of medical images appear in different forms from each other, the plurality of medical images may contain a common region of interest that may show the same lesion. According to the embodiment, the user may perform the interaction with respect to the volume and the slices through the user interface based on the visual identification mark that is shown in the common region of interest.

In the present document, the volume may be referred to as a three-dimensional image or a stereoscopic image. The volume may be a three-dimensional ultrasonic medical image that can be generated, for example, by photographing a specific part of a human body. The volume may be divided into a plurality of slices that represent planes obtained, for example, by cutting the human body along three body planes, which are perpendicular to each other.

In the present document, the slice may be referred to as a two-dimensional image or a cross sectional image. The slices, for example, may be two-dimensional planar images that are obtained by cutting the volume to correspond to planes parallel to three orthogonal axes (X, Y, Z) as shown in the MPR (multi-planar reconstruction) view.

According to the embodiment, a user interface may be provided, which enables the interaction between the user and the application for images based on the mark that is visually shown in the ROI within the associated volume and slices.

The expression "the volume and the slice are associated with each other" means that the slice is an image representing a cross section obtained by cutting the volume in a certain direction.

Therefore, even though it is not clearly specified, it may be obvious to those skilled in the art that a single volume has a plurality of slices. For example, those skilled in the art may easily understand that the slices may be provided along three orthogonal planes with respect to a single point in the volume. Furthermore, the expression "the slices are associated with each other" and its similar expressions mean that the associated slices represent different cross sections of the same volume.

In order to simplify the representation in the following description, the volume, the slice, and other slices represent the volume, the slice, and the slices, which are associated with each other, unless otherwise expressly specified.

The user interface provided according to the embodiment may allow the user to conveniently manipulate the ROI included in the volume and the slices based on a visual sign (that is, a mark).

The mark is a visual sign to uniquely identify each ROI. One or more marks may be displayed with respect to a single ROI. The mark may be formed by using text, symbols, and/or graphical representations. For example, the mark may contain unique identification information, such as a serial number, which uniquely identifies the ROI. In addition, the mark may further contain text, numbers, and/or symbols, which represent information for describing the ROI, such as the size, name, or malignancy of the ROI. Moreover, the mark may further contain pictures, signs, two-dimensional graphical representations, three-dimensional graphical representations, stationary icons, and/or moving icons, which intuitively indicate the characteristics of the ROI.

For example, the user may identify a specific ROI in a single slice through the user interface, according to the embodiment, and may then input marking information to place a mark in the inside, or outside, of the identified ROI (hereinafter, frequently referred to as "marking"). The marking information, for example, may contain the position where the mark is displayed in the slice, the form of the mark to be displayed, or information to be contained in the mark.

The ROI exists in the slice in which the user currently performs the interaction with the application (hereinafter, referred to as a "current slice") through the user interface. In addition, the ROI also exists in the volume that is associated with the current slice. Furthermore, the ROI exists in each of the other slices that are associated with the current slice.

It is assumed that the ROI that is identified in the current slice exists as being a "corresponding ROI" that is the same but has a different form in the associated volume and the other associated slices. This case, for example, may correspond to ultrasonic images obtained by photographing a breast region of a certain person for the early diagnosis of breast cancer, and the ROI may be a lesion found in the images.

According to the embodiment, the user interface may enable the interaction including user's automatic marking in the image. That is, in response to the user's marking action for a specific ROI of the current slice, the application may automatically generate and display the corresponding marks having the same identification information as the mark shown in the current slice with respect to the corresponding ROIs in the associated volume and other associated slices without a user's direct action.

The operation in which the same mark is automatically placed on the remaining slices when performing the marking with respect to the current slice is defined as tagging.

For example, the user may visually display a mark in the form of a text box, which contains identification information containing a unique serial number comprised of text, on the outside of a specific ROI of the current slice through the user interface. In this example, the displayed mark may be included in the slice in the form of an image that is overlaid on the slice. In response to the user's marking, the application automatically tags the mark comprised of text on the outside of the corresponding ROIs of the volume and other slices. In this case, the mark placed on a specific ROI and the mark tagged on the corresponding ROIs may have the same identification information, and may be visually displayed in the same text box form.

The user interface may allow the user to mark a specific ROI in the slice that is currently displayed on the screen, and may then allow the user to retrieve one or more of the associated volume and other slices to be displayed on the screen. As a result, the mark is automatically displayed in the corresponding ROI in the volume or slice, which is displayed on the screen.

In addition, the user interface provides a non-sequential search function based on the mark of the ROI. When the user selects the mark of a desired ROI in the current volume that is displayed on the screen, the application, in response thereto, displays, on the screen, several slices that are selected according to predetermined selection criteria among all of the slices including the ROI that is identified by the selected mark.

The selection criteria may be configured or specified by the user or other entities. For example, the selection criteria may contain: preferentially selecting the slice with which the user has previously interacted from the slices that contain the ROI identified by the selected mark; or preferentially selecting the slice that contains other ROIs from the slices that contain the ROI identified by the selected mark.

Furthermore, the user interface provides a mark arranging function for displaying all of the marks included in the volume on the screen without overlapping each other. A plurality of ROIs may be contained in the volume, and one or more marks may be displayed in each ROI. Each of the marks may be arranged so as not to overlap each other on the two-dimensional plane of the screen according to the user's gaze. Accordingly, the user's convenience may be provided when the user views the marks or selects a desired mark.

In this case, the user interface further provides a function of displaying, on the screen, all of the marks, which are included in the volume, without overlapping even when the volume is modified. The user may perform a modification operation to: rotate the volume, in which the marks have already been displayed, about a specific reference point; enlarge or reduce the volume; or move the volume. At this time, all of the marks in the volume may be automatically adjusted such that they are always displayed to the user without overlapping while being changed according to the modification of the volume.

In addition, the user interface may provide an ROI visualization function for visually distinguishing the ROI indicated by the selected mark from the periphery. The user may select a mark for identifying a desired ROI in the volume. Then, the properties of the pixel, such as brightness and/or chroma, may vary in the volume, for example, as it goes further from the ROI. This variation may be made such that the transparency of the periphery, which surrounds the ROI indicated by the selected mark, gradually increases in the volume. As a result, since the periphery except for the ROI becomes transparent, the ROI may be visually distinct from the periphery, and the user may be forced to gaze at the ROI.

FIG. 1A is a block diagram illustrating an embodiment of a user interface system for enabling mark-based interaction for images, according to an embodiment.

Referring to FIG. 1A, the user interface system 100 for enabling mark-based interaction for images may be implemented by a computing device. The computing device may include a storage medium, processing means, displaying means, input means, or the like. Any device for storing image information, such as two-dimensional images, three-dimensional images, still images, or videos, may be used for the storage medium without limitations. Any device for displaying, editing, associating, or combining image information, such as two-dimensional images, three-dimensional images, still images, or videos, may be used for the processing means without limitations. Any device for visually displaying image information, such as two-dimensional images, three-dimensional images, still images, or videos, may be used for the displaying means without limitations. Any device, such as a keyboard, a touch-sensitive input device, a mouse, or a microphone adopting a speech recognition function, for inputting information comprised of a combination of user's instructions, text, numbers, or symbols, may be used for the input means without limitations.

Therefore, the user interface system 100 for enabling mark-based interaction for images may be implemented, for example, by a single computing device, such as a tablet PC, a laptop PC, a desktop PC, a server system, or by a plurality of computing devices that interwork with each other.

Figure 2:
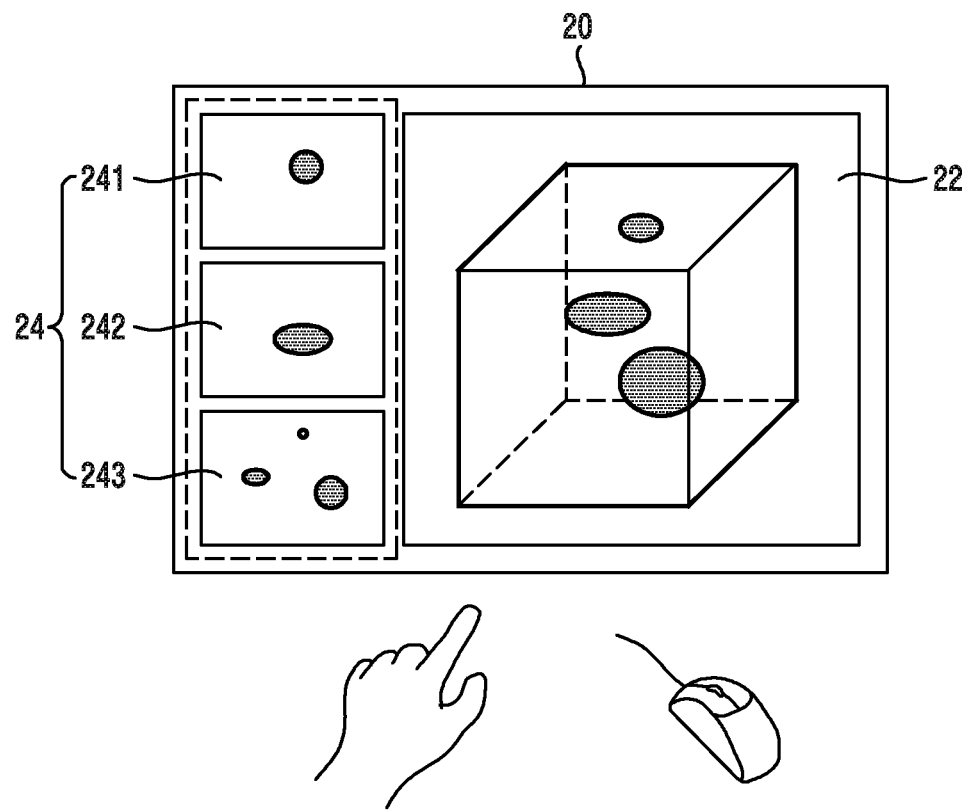
FIG. 2 is a view showing an embodiment of a user interface that is associated with the system of FIG. 1A.

FIG. 2 is a view showing an example of a user interface screen displayed on a display in the user interface system for manipulating the region of interest of an image, according to an embodiment.

Referring to FIG. 2, the interface screen 20 includes a volume region 22 and a slice region 24. A volume containing three ROIs that are simply shown in a gray circle and oval shape is displayed in the volume region 22. The slice region 24 contains different slice regions 241, 242, and 243. Each slice region shows a single slice. The illustration has been provided only as an example, and other screen configurations may be provided. For example, the slice region 24 may be displayed in a separated window from the volume region 22. As another example, the slice region 24 may be disposed on the right side of the volume region 22 rather than on the left side thereof, or may be disposed on the upper side or lower side thereof.

Referring back to FIG. 1A, according to the embodiment, the user interface system 100 for searching for the region of interest of a stereoscopic image may be configured to include components, such as an input unit 110, a mark generation unit 120, an image information database (DB) 130, an image search unit 140, a mark arrangement unit 150, an ROI visualization unit 160, a screen configuration unit 170, or an output unit 180.

The input unit 110 is a component that receives information input by the user through the input means (e.g., a keyboard, a mouse, a touch panel, or the like).

The mark generation unit 120 is a component that generates a mark to be displayed in the region of interest (ROI) that is contained in the volume and the slices representing the cross sections of the volume.

The mark generation unit 120 may generate a mark according to input information of the user. For example, it is assumed that the user views a volume, which is a three-dimensional ultrasonic image obtained by photographing a part of a breast of a human body, and slices associated therewith for a diagnosis of breast cancer. The user may view the slice or the volume, which is currently displayed on the screen, in order to thereby identify, as the region of interest (ROI), one or more lesions that, for example, may be a breast cancer tumor. The user may input an instruction to generate a mark that uniquely identifies the checked lesion (that is, the checked ROI). Then, the mark generation unit 120 may generate a mark containing information to uniquely identify each ROI according to the user's instruction, and may provide the same to be displayed on the screen to correspond to each ROI.

Figure 3:
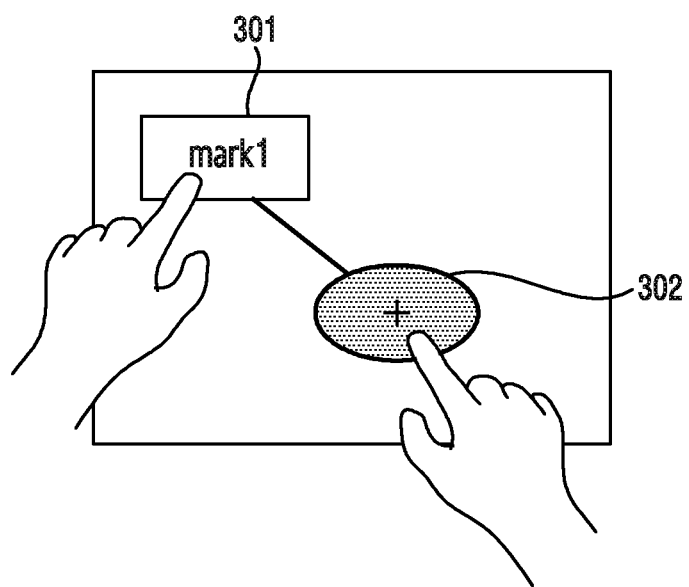
FIG. 3 is a view to explain an example of generating a mark in the region of interest in the user interface associated with the system of FIG. 1A.

FIG. 3 is a view to explain an example of generating the mark in the region of interest in the user interface system for manipulating the region of interest of an image, according to an embodiment.

Referring to FIG. 3, for example, the user may select the position where a mark is to be placed by using a finger touch or a mouse pointer, and may input information that is to be contained in the mark by using a physical keyboard or a virtual keyboard. FIG. 3 shows an example of a mark 301 in the form of a box outside the ROI and an example of a mark 302 that is a graphical representation in the form of an oval shape inside the ROI, respectively. The mark 301 that is in the form of a box may contain text information, such as unique identification information (e.g., a serial number) of the ROI to be identified, the size of the ROI, or the malignancy thereof. Although descriptive identification information is not contained, the graphic representation mark 302 may allow the user to intuitively recognize the approximate shape and relative size of the ROI.

As described above, one or more marks may be visually displayed in a single ROI. The mark may be displayed in the inside/outside of the ROI regardless of its position as long as the mark is displayed to be associated with the ROI. The mark may contain a text representation and/or a graphical representation, as well as the identification information to uniquely identify the ROI. The text representation may be comprised of a combination of letters, numbers, and symbols to describe the ROI. The graphical representation may contain various graphical representations, such as pictures, symbols, two-dimensional/three-dimensional graphical representations, and/or the stationary icons, or moving icons, which intuitively represent the ROI.

Referring back to FIG. 1A, furthermore, the mark generation unit 120 may generate and display the mark (or may perform marking) in the ROI of the current slice, and may then automatically generate and display marks (or may perform tagging) in the corresponding ROIs in other slices and the volume. In this case, the tagged mark has the same identification information as the marking-performed mark. That is, the tagged marks in other slices identify the same ROI as (or the ROI equivalent to) the ROI identified by the mark in the current slice.

Information related to the mark generated by the mark generation unit 120, the ROI, the volume, and the slices may be stored in the image information database (DB) 130.

Thereafter, when other slices including the ROI, which is tagged with the mark by the mark generation unit 120, are retrieved by the user to be displayed on the screen, the screen configuration unit 170, for example, may refer to the image information DB 130, and may provide the retrieved slices to the output unit 180 to display the same on the screen. At this time, the retrieved slice may be displayed on the screen while the mark previously tagged by the mark generation unit 120 is shown in the slice.

Figure 4:
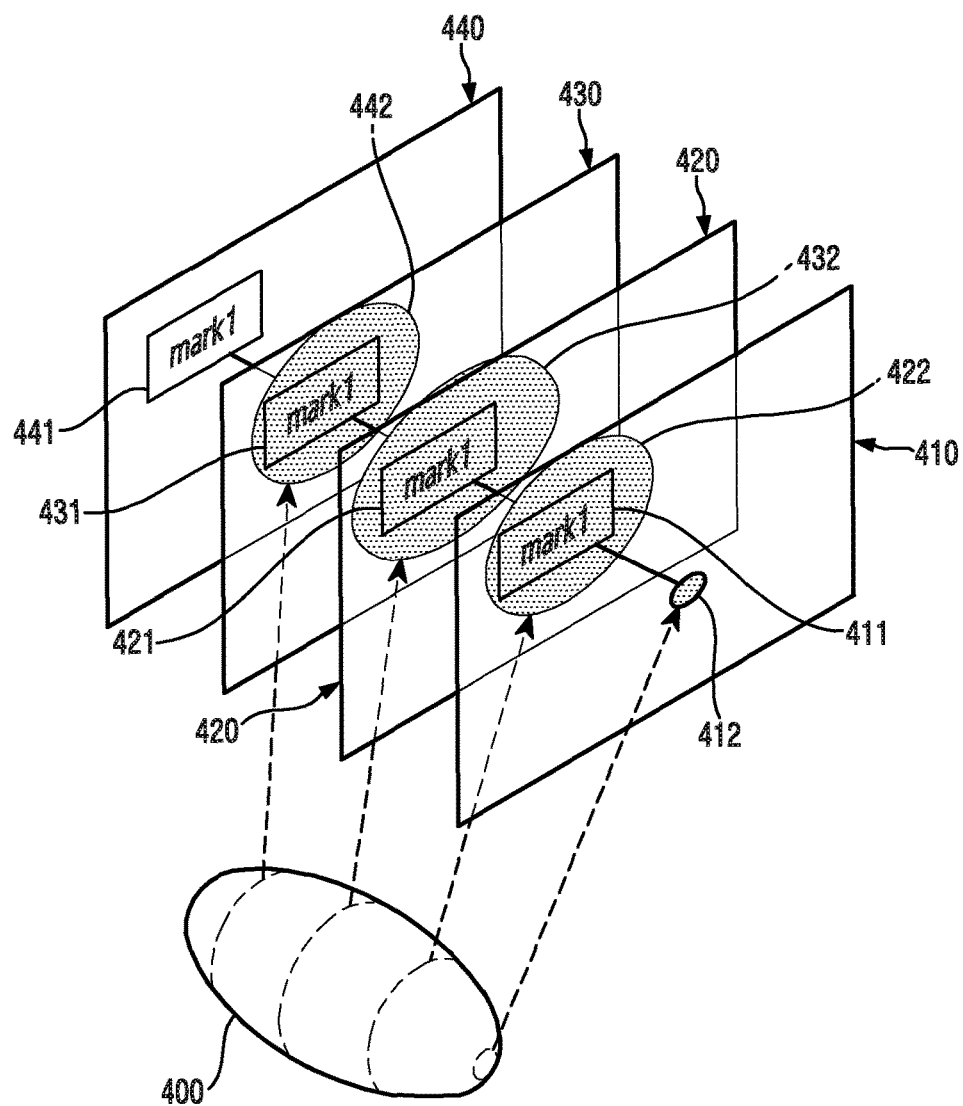
FIG. 4 is a view to explain a mark that is displayed in the region of interest of the slices that are associated with the region of interest of the volume in the user interface associated with the system of FIG. 1A.

FIG. 4 is a view to explain a mark that is displayed in the region of interest of the slices that are associated with the ROI of the volume in the user interface system for manipulating the region of interest of an image, according to an embodiment.

Referring to FIG. 4, the ROI 400 in the form of a three-dimensional rugby ball (that is, in a volume form) is illustrated. Four slices 410, 420, 430, and 440 are illustrated, which represent, in part, cross sections obtained by cutting the three-dimensional ROI 400. The slices 410, 420, 430, and 440 contain marks 411, 421, 431, and 441 in the form of a text box and two-dimensional graphic marks 412, 422, 432, and 442 in the form of an oval shape, respectively. The slices 410, 420, 430, and 440 contain the same ROI 400. However, the slices 410, 420, 430, and 440 have two-dimensional graphic marks 412, 422, 432, and 442 in the form of an oval shape, which have different sizes, as well as the marks 411, 421, 431, and 441 in the form of the same text box.

As described above, it is assumed that the user displays a single slice 410 on the screen, and then generates and displays the mark 411 in a text form including the unique identification information with respect to the ROI corresponding to the ROI 400 and a two-dimensional mark 412 in the form of a small oval shape, which intuitively represents the size and shape of the ROI. Then, the mark generation unit 120 may automatically tag the marks 421, 431, and 441 in the text form containing the same unique identification information on the corresponding ROI included in other slices 420, 430, and 440 obtained by cutting the ROI 400, and may further tag the two-dimensional marks 422, 432, and 442 in the form of an oval shape, which have different sizes to intuitively represent the size and shape of the ROI.

In addition, the user may add marking information on the same ROI in one or more slices in order to improve the accuracy of the tagging. In this case, the tagging operation for the corresponding ROI may be performed by reflecting all of the input information of each slice. Afterwards, the correction operation of tagging information may be performed in a similar manner. For example, when the user corrects the mark for a specific ROI with respect to one or more slices, the tagging operation may be re-executed by reflecting the same in order to thereby correct all of the tagging information.

Thereafter, for example, it is assumed that the user retrieves the slice 420 to be displayed on the screen. Then, although the user has never marked the corresponding ROI, the slice 420 displayed on the screen contains the marks 421 and 422 that are automatically tagged on the corresponding ROI.

Figure 1B:
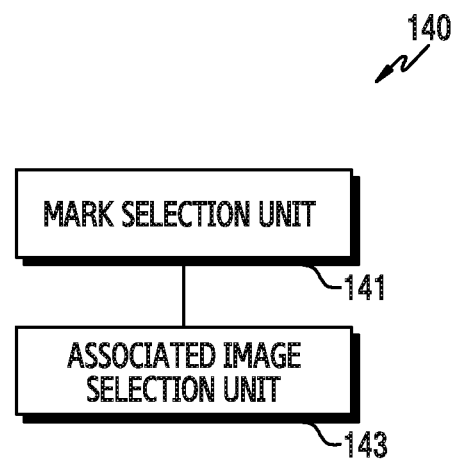
FIG. 1B is a block diagram to explain an image search unit in more detail in the system of FIG. 1A.

FIG. 1B is a block diagram to explain the image search unit in more detail in the system of FIG. 1A.

Referring to FIGS. 1A and 1B, the image search unit 140 enables a non-sequential search for a desired slice among the slices having the mark. The image search unit 140 may include a mark selection unit 141 and an associated image selection unit 143.

The mark selection unit 141 allows the user to select a mark that identifies a desired ROI, and receives a mark selected by the user. In the state in which the slice or the volume is displayed on the screen, the user may select the mark for identifying a desired ROI in the displayed slice or volume through the input means. The associated image selection unit 143 selects slices according to predetermined selection criteria from the slices that have the ROI corresponding to the ROI identified by the mark selected by the user. In addition, the associated image selection unit 143 may provide the selected slices to the screen configuration unit 170 to display the same on the screen.

According to the embodiment, default values set by the system manufacturer or supplier may be used for the selection criteria for selecting the slice by the associated image selection unit 143. Alternatively, the selection criteria may be configured by the user through a configured process provided by the system. For example, the user may configure the selection criteria as preferentially selecting a slice corresponding to the MPR (Multi-Planar Reconstruction) view based on the ROI identified by the selected mark. Alternatively, the user may configure the selection criteria as preferentially selecting the slice with which the user (or another user) has previously interacted. Alternatively, the user may configure the selection criteria as preferentially selecting the slice that contains as many other ROIs as possible in the volume. Such criteria may enable a non-sequential search for a specific ROI and a preferential search for the slice containing the ROI that corresponds, or is highly similar, to the ROI that is under consideration.

Figure 5A:
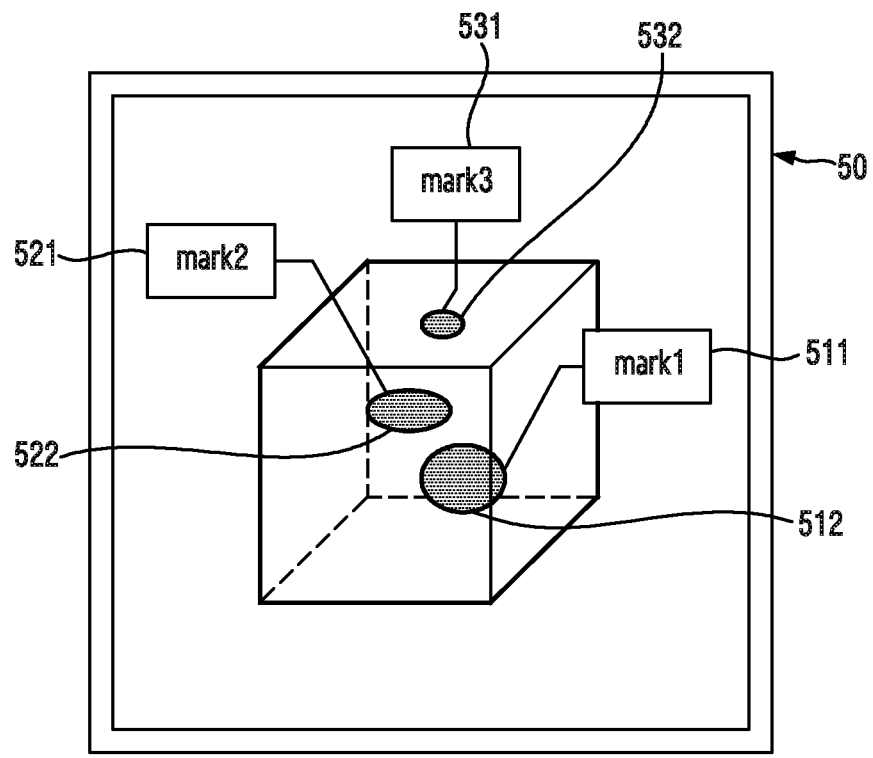
FIG. 5A is a view to explain an example in which a user selects a mark displayed in the region of interest of the volume and searches for the slices in the user interface associated with the system of FIG. 1A.

FIG. 5A is a view to explain an example in which the user selects the mark displayed in the region of interest of the volume and searches for the slices in the user interface associated with the system of FIG. 1A.

Referring to FIG. 5A, a volume 50 is illustrated on the screen, wherein marks 511, 521, and 531 are visually displayed in the form of a text box that contains unique identification information on each of three ROIs 512, 522, and 532. For example, the user may select a desired ROI 512 by touching one (e.g., the mark 511) of the marks with a finger. Then, the selection may be detected by the mark selection unit 141 of the image search unit 140, and the slices having a high similarity may be automatically searched for according to the selection criteria configured by the associated image selection unit 143.

Figure 5B:
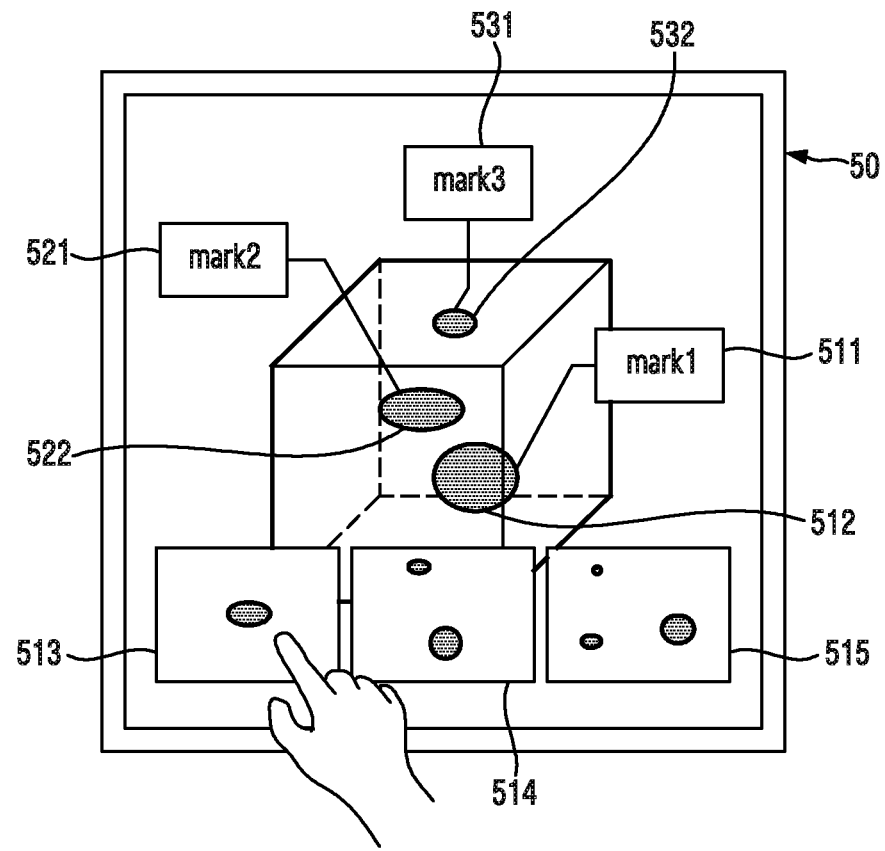
FIG. 5B is a view to explain an example in which three different slices are searched for, which correspond to the mark selected in FIG. 5A.

FIG. 5B is a view to explain an example in which three different slices are searched for, which correspond to the mark selected in FIG. 5A.

Referring to FIG. 5B, the search result for the mark selected by the user in FIG. 5A is illustrated. As shown in the drawing, three slices 513, 514, and 515 may be selected to be displayed on the screen. The three displayed slices 513, 514, and 515 may be slices that represent different cross sections of the ROI 512 that is identified by the mark 511 selected by the user.

Figure 6A:
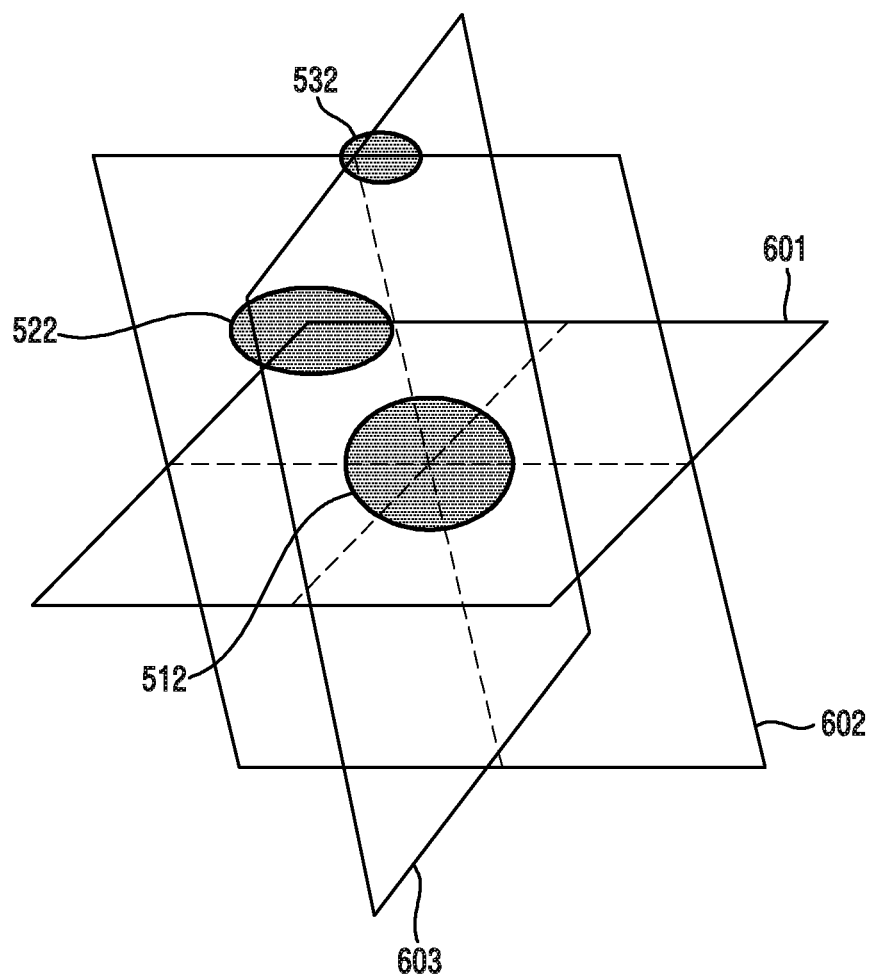
FIG. 6A is a view to explain criteria for selecting slices to be searched for when searching for the slices by using the mark displayed in the region of interest of the volume in the user interface associated with the system of FIG. 1A.

FIG. 6A is a view to explain the criteria for selecting slices to be searched for when searching for the slices by using the mark displayed in the region of interest of the volume in the user interface associated with the system of FIG. 1A.

Referring to FIG. 6A, it is assumed that the user selects a mark that identifies the ROI 512. In this case, the slices 601, 602, and 603 may be selected, which show three orthogonal planes based on the selected ROI 512. Furthermore, the selection criteria may include selecting a cross section that has as many ROIs as possible, as well as selecting a cross section that is obtained by randomly cutting the volume based on the selected ROI 512.

Figure 6B:
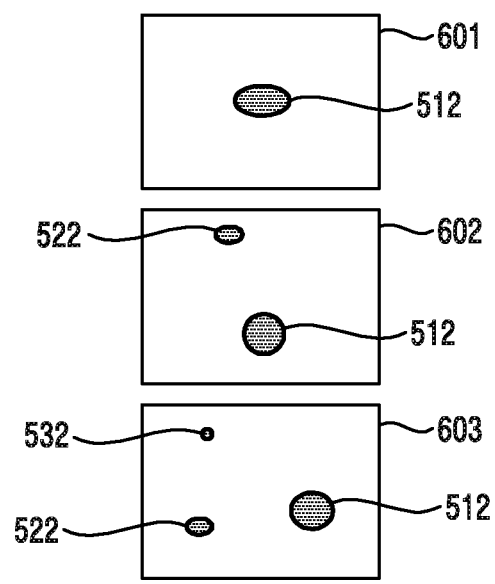
FIG. 6B illustrates slices according to the selection criteria of FIG. 6A.

FIG. 6B illustrates slices according to the selection criteria of FIG. 6A.

Referring to FIG. 6B, the selected slices 601, 602, and 603 may contain, in part, other ROIs 522 and 532, as well as the selected ROI 512. These slices 601, 602, and 603 have been selected according to the criteria for selecting the slice that has as many ROIs as possible.

Figure 1C:
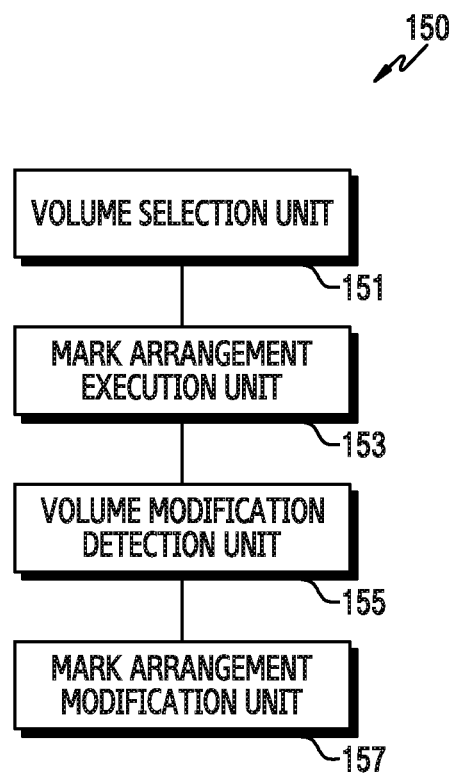
FIG. 1C is a block diagram to explain a mark arrangement unit in more detail in the system of FIG. 1A.

FIG. 1C is a block diagram to explain the mark arrangement unit in more detail in the system of FIG. 1A.

Referring to FIGS. 1A and 1C, the mark arrangement unit 150 is a component that displays the marks included in the volume on the screen without overlapping each other. One or more ROIs may exist in the volume, and one or more marks may be displayed in each ROI. Therefore, when the volume is displayed on the screen, a plurality of marks may be mixed. The mark arrangement unit 150 performs a function of arranging the marks on the two-dimensional screen to not overlap each other. Accordingly, the user may easily select a mark that identifies a desired ROI so that the user convenience may be improved.

The mark arrangement unit 150 may include a volume selection unit 151, a mark arrangement execution unit 153, a volume modification detection unit 155, and a mark arrangement modification unit 157. The volume selection unit 151 allows the user to select a volume of which marks are to be arranged, and receives the user's selection through the input unit 110. The mark arrangement execution unit 153 arranges, on the screen, all of the marks included in the selected volume so as not to overlap each other. The positions of the arranged marks may be provided to the screen configuration unit 170 to then be displayed together with the volume on the screen.

In addition, if the volume displayed on the screen is modified by enlarging, reducing, rotating, or moving the same, the volume modification detection unit 155 may detect the same. The mark arrangement modification unit 157 may arrange the marks, which have been previously arranged, to be displayed without overlapping while the marks are not modified according to the modification of the volume, and/or may arrange the marks to be displayed without overlapping while the marks are modified according to the modification of the volume.

Figure 7A:
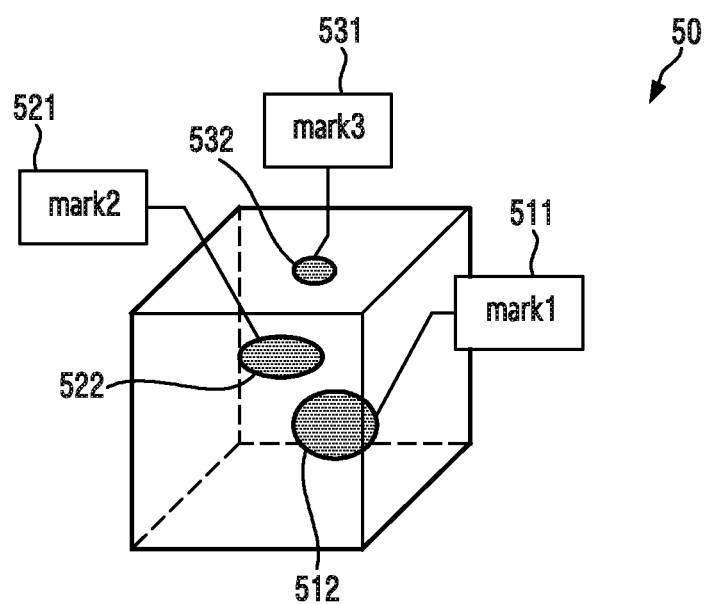
FIG. 7A is a view to explain an example in which the marks are displayed in the region of interest without overlapping each other when the volume is modified in the user interface associated with the system of FIG. 1A.

FIG. 7A is a view to explain an example in which the marks are displayed in the region of interest without overlapping each other when the volume is modified in the user interface associated with the system of FIG. 1A. Referring to FIG. 7A, the volume 50 contains three ROIs 512, 522, and 532, and each ROI shows a single mark 511, 521, or 531. When this volume 50 is displayed on the screen, the mark arrangement unit 150 may arrange the marks 511, 521, and 513 to not overlap each other. The user may touch the bottom left of the volume 50 with a finger to draw a small circle in order to thereby rotate the volume 50.

Figure 7B:
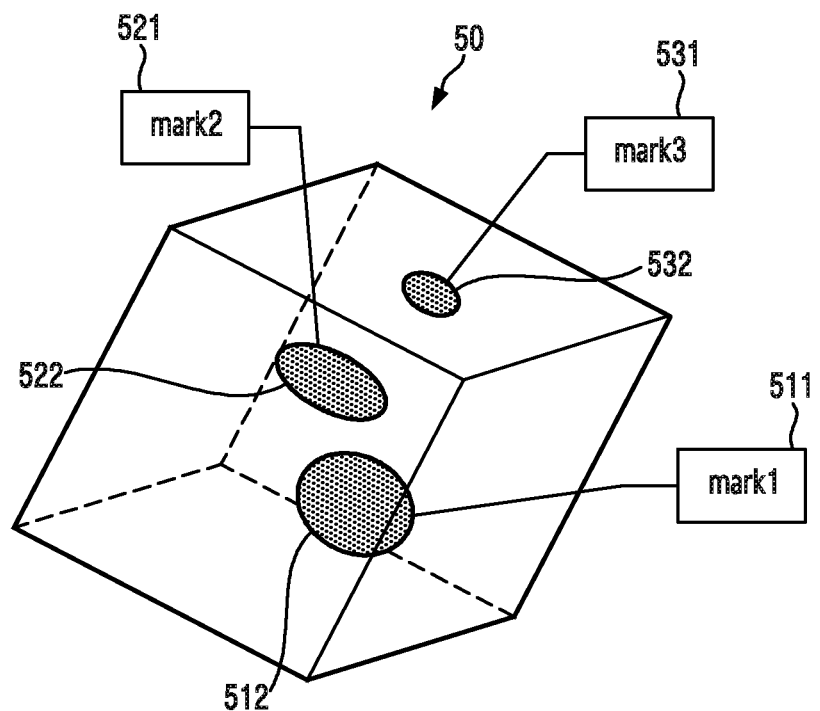
FIG. 7B is a view to explain an example in which the marks are displayed to not overlap each other when the volume is modified in FIG. 7A.

FIG. 7B is a view to explain an example in which the marks are displayed to not overlap each other when the volume is modified in FIG. 7A.

Referring to FIG. 7B, when the volume is rotated in FIG. 7A, the mark arrangement unit 150 may rearrange the marks 511, 521, and 513 by modifying the marks 511, 521, and 513 to maintain the horizontal state in order to facilitate a user's viewing and to be associated with each corresponding ROI. As a result, as shown in the drawing, although the volume 50 is rotated to be tilted, the marks 511, 521, and 531 may be rearranged to maintain its horizontal state.

Figure 1D:
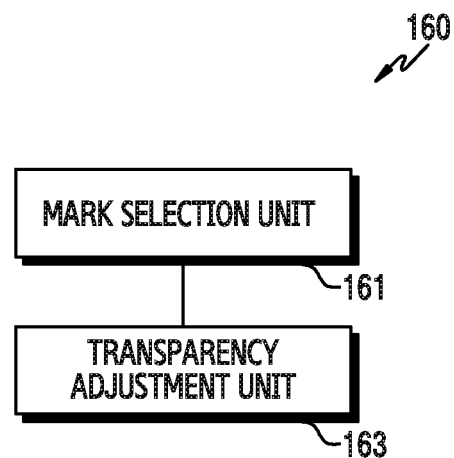
FIG. 1D is a block diagram to explain an ROI visualization unit in more detail in the system of FIG. 1A.

FIG. 1D is a block diagram to explain an ROI visualization unit in more detail in the system of FIG. 1A.

Referring to FIGS. 1A and 1D, the ROI visualization unit 160 is a component to visualize the selected ROI, or the ROI identified by the selected mark, to be visually distinct from the periphery among the ROIs in the volume. The ROI visualization unit 160 may include a mark selection unit 161 and a transparency adjustment unit 163.

The mark selection unit 161 may allow the user to select a desired mark from the marks included in the volume displayed on the screen, and may receive information selected by the user. The transparency adjustment unit 163 is a component that modifies the ROI, which is identified by the mark selected by the user, to be distinct from the periphery. According to the embodiment, the transparency adjustment unit 163 may modify image data representing the volume such that the transparency of the peripheral area surrounding the ROI identified by the selected mark gradually increases as it goes further from the selected ROI or from the ROI identified by the selected mark.

Figure 8A:
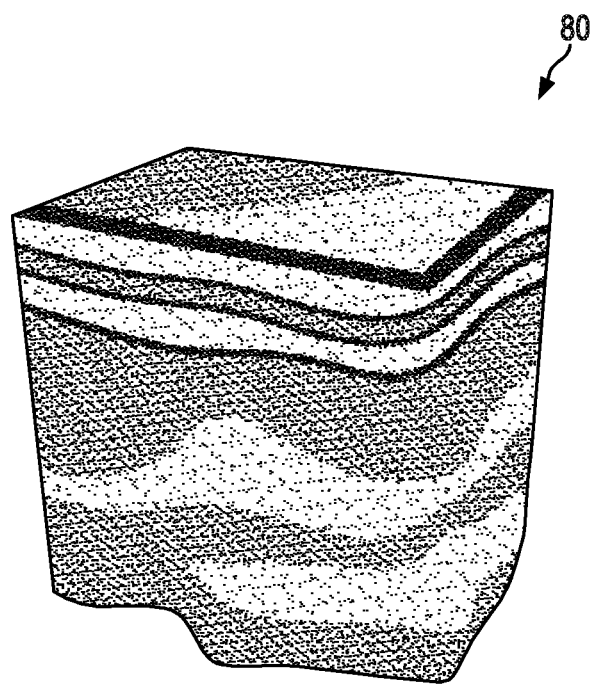
FIG. 8A is a view illustrating an example in the case where the volume is a three-dimensional ultrasonic image in the user interface associated with the system of FIG. 1A.

FIG. 8A is a view illustrating an example in the case where the volume is a three-dimensional ultrasonic image in the user interface associated with the system of FIG. 1A.

Referring to FIG. 8A, a volume 80 is illustrated, which may be three-dimensional ultrasonic image. The illustrated volume 80, for example, may be a stereoscopic image obtained by photographing a specific region, such as a breast of a human body, by using ultrasonic waves. The volume 80 may be a complicated image that includes an anatomical structure, such as skin, a mammary gland, fat, muscles, or ribs. The user, for example, may identify the region of interest, such as lesions, in the complicated structure by using an image processing application, such as a CAD (computer aided diagnosis).

Figure 8B:
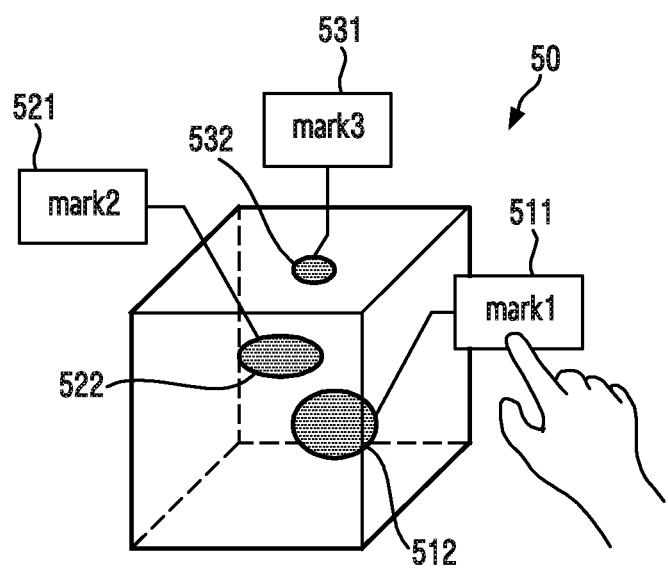
FIG. 8B is a view illustrating an example in which a user selects one mark among the region of interest and the marks, which are contained in the volume of FIG. 8A.

FIG. 8B is a view illustrating an example in which the user selects one mark among the region of interest and the marks, which are contained in the volume of FIG. 8A.

FIG. 8B illustrates an example in which the volume 80 of FIG. 8A has been modified to the volume 50 that contains three ROIs 512, 522, and 532 and marks 511, 521, and 532 that are shown in the respective ROIs. It is assumed that the user displays the volume 50 on the screen and selects the mark 511 in order to visualize the same to be visually distinct from the periphery.

Figure 8C:
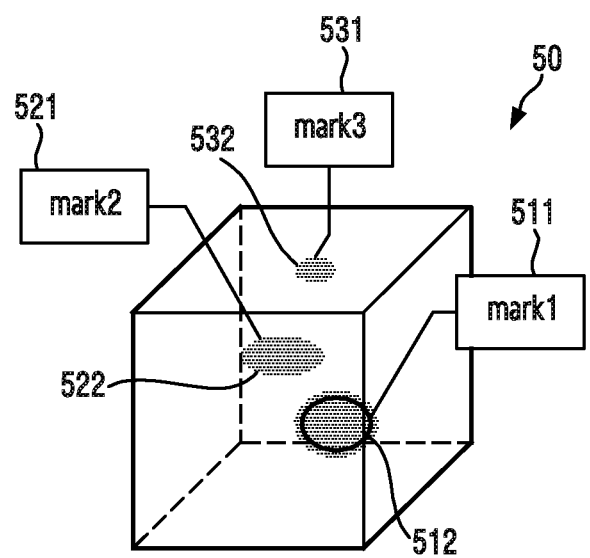
FIG. 8C is a view to explain an example of visualization to improve the visibility of the region of interest indicated by the mark selected in FIG. 8B.

FIG. 8C is a view to explain an example of visualization to improve the visibility of the region of interest indicated by the mark selected in FIG. 8B.

Referring to FIG. 8C, as shown in the drawing, the transparency adjustment unit 163 may increase the transparency of the volume 50 as it goes further from the ROI 512 identified by the selected mark 511. According to this, the convenience may be provided to allow the user to view a desired ROI more intensively.

Hereinafter, a user interface providing method for manipulating the region of interest of an image, according to the embodiment, will be described with reference to FIGS. 9 to 12. The user interface providing method for manipulating the region of interest of an image, according to the embodiment, may be stored in a computer-readable storage medium in the form of, for example, a computer-executable instruction, a module, a routine, a program, or software, and thereafter, may be read and executed by the processor in order to thereby be implemented by a computing device for interacting with the user through a display device and an input device at the same time.

Figure 9:
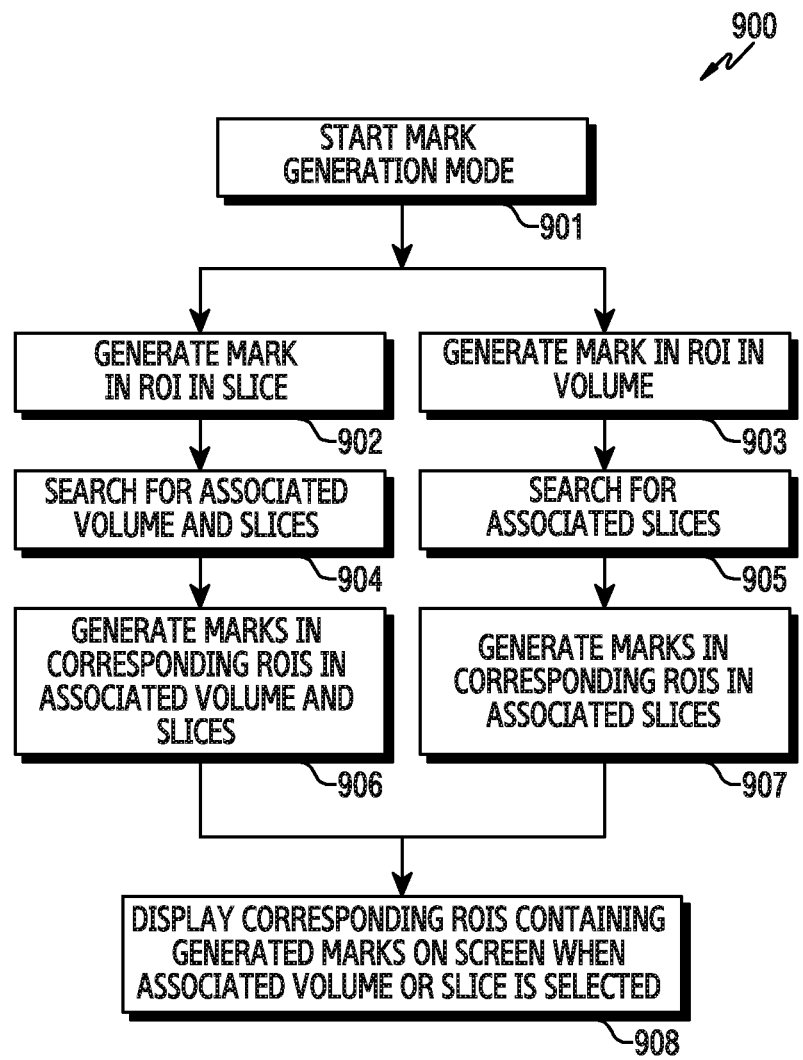
FIG. 9 is a flowchart illustrating an example of a mark generation operation in an example of a user interface providing method for enabling the mark-based interaction for images.

FIG. 9 is a flowchart illustrating an example of a mark generation operation in the user interface providing method for manipulating the region of interest of an image, according to an embodiment.

FIG. 9 illustrates a mark generation operation 900 in the user interface providing method for manipulating the region of interest of an image, according to the embodiment.

For example, the user may select a menu, or enter an instruction, to start a mark generating mode in a computing device that implements the user interface providing method for manipulating the region of interest of an image, according to the embodiment (901). Next, the user may select a desired ROI in the slice, and may input information or instructions required for the mark generation so that the mark may be generated and displayed (902). Thereafter, the computing device searches for an associated volume and slices, which contain the corresponding ROI, based on the marked ROI (904). Then, the computing device generates and displays a mark that contains the same identification information on the corresponding ROIs in the associated volume and slices (906). Thereafter, when the user selects the associated volume and slice to display the same on the screen, the selected volume and slice may be displayed on the screen while the mark is displayed on the corresponding ROI (908).

Meanwhile, after the mark generating mode starts (901), the user may select a desired ROI in the volume, and may input information or instructions required for the mark generation so that the mark may be generated and displayed (903). Next, the computing device searches for associated slices, which contain the corresponding ROI, based on the marked ROI (905). Then, the computing device generates and displays a mark that contains the same identification information on the corresponding ROI in the associated slices (907). Thereafter, when the user selects the associated slice to display the same on the screen, the selected slice may be displayed on the screen while the mark is displayed on the corresponding ROI (908).

Figure 10:
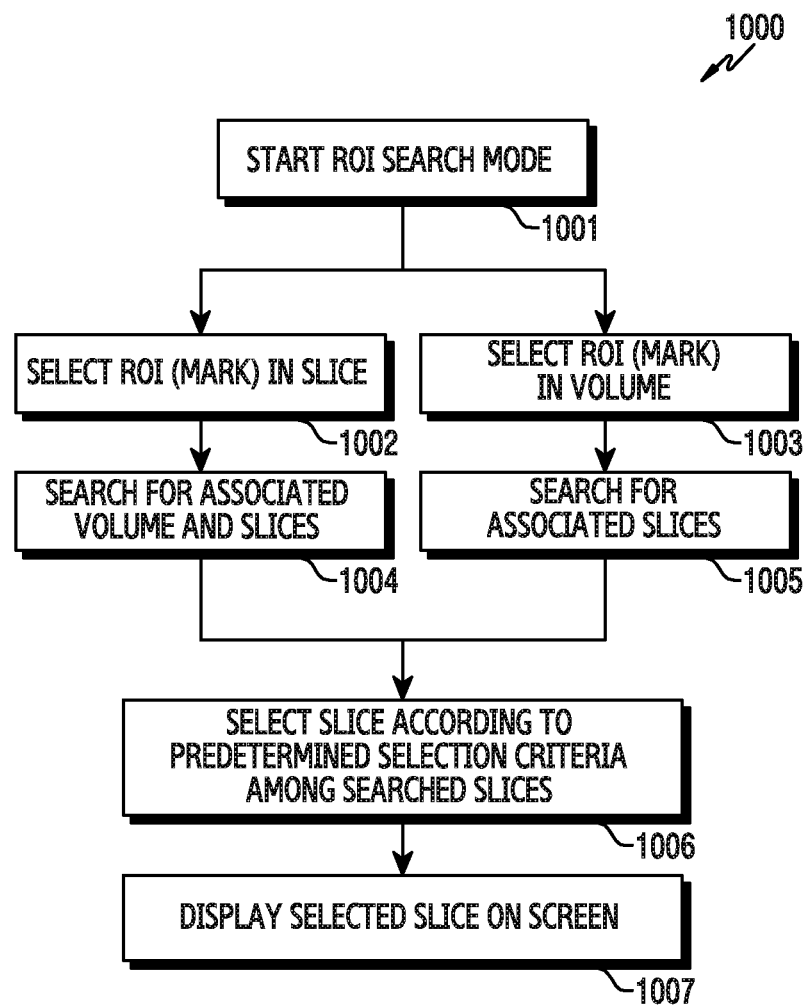
FIG. 10 is a flowchart illustrating an example of a mark-based search operation in an example of a user interface providing method for enabling the mark-based interaction for images.

FIG. 10 is a flowchart illustrating an example of a mark-based search operation in the user interface providing method for manipulating the region of interest of an image, according to an embodiment.

FIG. 10 illustrates a mark-based search operation 1000 in the user interface providing method for manipulating the region of interest of an image, according to the embodiment.

For example, the user may select a menu or enter an instruction to start, for example, an ROI search mode in a computing device that implements the user interface providing method for manipulating the region of interest of an image, according to the embodiment (1001). Next, the user may select a desired ROI or a desired mark in the slice (1002). Thereafter, the computing device searches for an associated volume and slices, which contain the corresponding ROI, based on the selected mark or ROI (1004). Thereafter, the computing device may select a slice according to predetermined selection criteria among the associated volume and slices (1006), and may display the same on the screen (1007).

At this time, the selection criteria may contain: preferentially selecting the slice with which the user has previously interacted from the slices that contain the ROI identified by the selected mark; or preferentially selecting the slice that contains other ROIs from the slices that contain the ROI identified by the selected mark.

Meanwhile, after the ROI search mode starts (1001), the user may select a desired ROI or a desired mark in the volume (1003). Next, the computing device searches for associated slices containing the corresponding ROI based on the selected mark or ROI (1005). Then, the computing device may select a slice according to predetermined selection criteria among the associated volume and slices (1006), and may display the same on the screen (1007).

Figure 11:
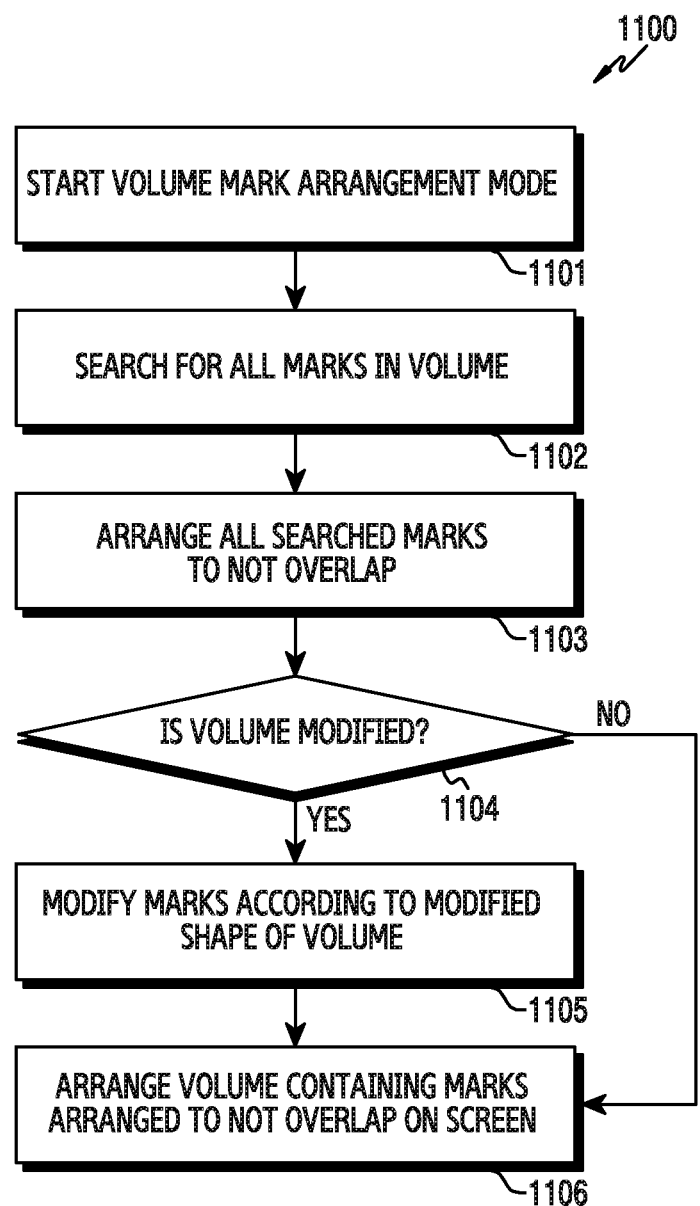
FIG. 11 is a flowchart illustrating an example of an operation of displaying the marks to not overlap each other in the volume in an example of a user interface providing method for enabling the mark-based interaction for images.

FIG. 11 is a flowchart illustrating an example of an operation of displaying the marks to not overlap each other in the stereoscopic image in the user interface providing method for manipulating the region of interest of an image, according to an embodiment.

FIG. 11 illustrates a mark arrangement operation 1100 in the user interface providing method for manipulating the region of interest of an image, according to the embodiment.

For example, the user may select a menu, or enter an instruction, to start, for example, a volume mark arrangement mode in a computing device that implements the user interface providing method for manipulating the region of interest of an image, according to the embodiment (1101). Thereafter, all of the marks in the volume are searched for (1102). All of the searched marks may be arranged to not overlap each other on the two-dimensional screen (1103). Next, it is determined whether or not the volume is modified by rotating, moving, reducing, or enlarging the same (1104). If the volume is not modified (No in operation 1104), the volume is displayed on the screen, which includes the marks that are arranged to not overlap each other (1106). If the volume is modified (Yes in operation 1104), the computing device may modify the marks or may change the positions thereof according to the modified shape of the volume in order to thereby rearrange the marks to not overlap each other (1105), and to then be displayed on the screen (1106).

Figure 12:
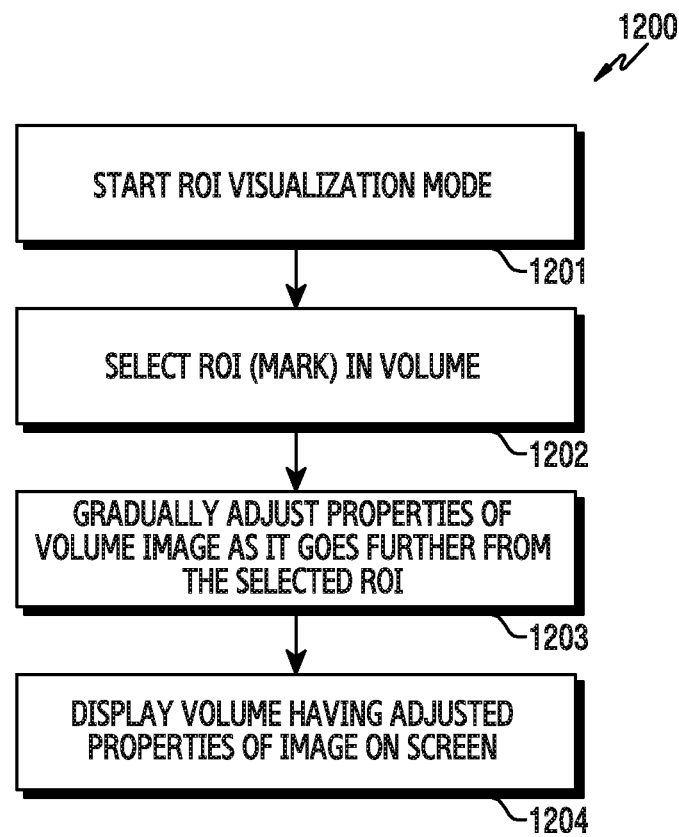
FIG. 12 is a flowchart illustrating an example of an ROI visualization operation in the volume in an example of a user interface providing method for enabling the mark-based interaction for images.

FIG. 12 is a flowchart illustrating an example of an ROI visualization operation in the stereoscopic image in the user interface providing method for manipulating the region of interest of an image, according to the embodiment.

FIG. 12 illustrates an ROI visualization operation 1200 in the user interface providing method for manipulating the region of interest of an image, according to the embodiment.

For example, the user may select a menu, or enter an instruction, to start, for example, an ROI visualization mode in a computing device that implements the user interface providing method for manipulating the region of interest of an image, according to the embodiment (1201). Thereafter, the user selects a desired mark or a desired ROI in the volume (1202). Next, the properties of the volume image may be adjusted such that the transparency gradually increases as it goes further from the ROI identified by the selected mark or from the selected ROI (1203). Thereafter, the adjusted volume may be displayed on the screen (1204).

The apparatuses, components, and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The processes, functions, and methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, Wi-Fi, etc.). In addition, functional programs, codes, and code segments for accomplishing the example disclosed herein can be construed by programmers skilled in the art based on the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A user interface system for enabling mark-based interaction for images including a volume that is a three-dimensional image and slices that are two-dimensional images representing cross sections of the volume, the user interface system comprising:
   a memory configured to store instructions; and
   at least one processor, upon executing the stored instructions, configured to:
      receive a user input that is associated with a region of interest (ROI) in one image among the images,
      generate, in response to the user input, a mark comprising identification information for identifying the ROI,
      place the generated mark on the ROI included in the one image,
      automatically generate at least one mark, to be tagged to at least one ROI included in at least one other image rather than the one image, based on the identification information, wherein the at least one other image comprises an ROI corresponding to the ROI included in the one image,
      tag the generated at least one mark on the at least one ROI included in the at least one other image,
      adjust image data representing the volume such that a selected ROI or an ROI identified by a selected mark among ROIs included in the volume is visually distinct from a periphery, and
      modify the image data representing the volume such that a transparency of a peripheral area surrounding the selected ROI or the ROI identified by the selected mark gradually increases as it goes further from the selected ROI or the ROI identified by the selected mark.

2. The user interface system according to claim 1, wherein the mark comprises at least one of text representations comprised of a combination of text, numbers, or symbols, which describe the ROI, pictures, signs, and graphical representations, which intuitively represent the ROI.

3. The user interface system according to claim 1, wherein the mark is generated in the inside, or the outside, of the ROI.

4. The user interface system according to claim 1, wherein the at least one processor is further configured to:
   control a display to display the generated at least one mark on the at least one other image.

5. The user interface system according to claim 1, wherein the at least one processor is further configured to:
   receive user input information for selecting a mark of the ROI in the one image among the images, select at least one slice according to predetermined selection criteria from the slices comprising the ROI identified by the mark that is selected by the user input information, and display the selected at least one slice on a screen.

6. The user interface system according to claim 5, wherein the predetermined selection criteria includes at least one of: preferentially selecting the at least one slice corresponding to a multi-planar reconstruction (MPR) view based on the ROI identified by the selected mark, preferentially selecting the at least one slice with which the user has previously interacted, and preferentially selecting the at least one slice that comprises as many other ROIs as possible in the volume.

7. The user interface system according to claim 1, wherein the at least one processor is further configured to display marks included in the volume to not overlap each other.

8. The user interface system according to claim 7,
wherein the volume is modified by enlarging, reducing, rotating, or moving the same, and
wherein the at least one processor is further configured to display the marks to not overlap each other while modifying the marks according to the modification of the volume.

9. A user interface providing method for enabling mark-based interaction for images including a volume that is a three-dimensional image and slices that are two-dimensional images representing cross sections of the volume, the method comprising:
receiving a user input that is associated with a region of interest (ROI) in one image among the images;
generating, in response to the user input, a mark comprising identification information for identifying the ROI;
placing the generated mark on the ROI included in the one image;
automatically generating at least one mark, to be tagged to at least one ROI included in at least one other image rather than the one image, based on the identification information, wherein the at least one other image comprises an ROI corresponding to the ROI included in the one image;
tagging the generated at least one mark on the at least one ROI included in the at least one other image;
adjusting image data representing the volume such that a selected ROI or an ROI identified by a selected mark among ROIs included in the volume is visually distinct from a periphery; and
modifying the image data representing the volume such that a transparency of a peripheral area surrounding the selected ROI or the ROI identified by the selected mark gradually increases as it goes further from the selected ROI or the ROI identified by the selected mark.

10. The method according to claim 9, wherein the mark comprises at least one of text representations comprised of a combination of text, numbers, or symbols, which describe the ROI, pictures, signs, and graphical representations which intuitively represent the ROI.

11. The method according to claim 9, wherein the mark is generated in the inside, or the outside, of the ROI.

12. The method according to claim 9, further comprising:
displaying the generated at least one mark on the at least one other image.

13. The method according to claim 9, further comprising:
receiving user input information for selecting a mark of the ROI in the one image among the images;
selecting at least one slice according to predetermined selection criteria from the slices comprising the ROI identified by the mark that is selected by the user input information; and
displaying the selected at least one slice on a screen.

14. The method according to claim 13, wherein the predetermined selection criteria include at least one of:
preferentially selecting the at least one slice corresponding to a multi-planar reconstruction (MPR) view based on the ROI identified by the selected mark,
preferentially selecting the at least one slice with which the user has previously interacted, and
preferentially selecting the at least one slice that comprises as many other ROI as possible in the volume.

15. The method according to claim 9, further comprising:
displaying marks included in the volume to not overlap each other.

16. The method according to claim 15, further comprising:
displaying, when the volume displayed on the screen is modified by enlarging, reducing, rotating, or moving the same, the marks to not overlap each other while modifying the marks according to the modification of the volume.

* * * * *